US009278190B2

(12) United States Patent
Sina et al.

(10) Patent No.: US 9,278,190 B2
(45) Date of Patent: Mar. 8, 2016

(54) CATHETER FOR INTRALUMINAL TREATMENT, METHOD FOR MAKING THE SAME AND APPARATUS FOR MAKING A TOOL

(75) Inventors: Achille Sina, Roncadelle (IT); Giovanni Scalvini, Roncadella (IT)

(73) Assignee: Medtronic Vascular, Inc., Santa Rosa, CA (US)

( * ) Notice: Subject to any disclaimer, the term of this patent is extended or adjusted under 35 U.S.C. 154(b) by 131 days.

(21) Appl. No.: 13/519,977

(22) PCT Filed: Dec. 30, 2009

(86) PCT No.: PCT/IT2009/000597
§ 371 (c)(1),
(2), (4) Date: Jun. 29, 2012

(87) PCT Pub. No.: WO2011/080778
PCT Pub. Date: Jul. 7, 2011

(65) Prior Publication Data
US 2012/0273120 A1    Nov. 1, 2012

(51) Int. Cl.
*A61M 29/02* (2006.01)
*B29C 65/00* (2006.01)
*B29C 65/16* (2006.01)
*A61M 25/00* (2006.01)
*A61M 25/10* (2013.01)

(52) U.S. Cl.
CPC ....... *A61M 25/0023* (2013.01); *A61M 25/1006* (2013.01); *A61M 25/1027* (2013.01); *Y10T 156/1002* (2015.01)

(58) Field of Classification Search
CPC ............... A61M 25/0023; A61M 25/1027; A61M 25/1006
USPC ............ 604/96.01, 101.01–101.05, 103.01, 604/103.07; 156/196
See application file for complete search history.

(56) References Cited

U.S. PATENT DOCUMENTS

| | | | | |
|---|---|---|---|---|
| 5,078,727 A * | 1/1992 | Hannam et al. | ............... | 606/194 |
| 5,683,410 A * | 11/1997 | Samson | ........................ | 606/194 |
| 5,820,613 A * | 10/1998 | Van Werven-Franssen et al. | ............................. | 604/527 |
| 5,968,012 A * | 10/1999 | Ren et al. | .................... | 604/96.01 |
| 6,488,658 B1 * | 12/2002 | Long | ............................. | 604/113 |
| 6,746,392 B2 * | 6/2004 | Stiger et al. | ........................ | 600/3 |
| 2002/0121472 A1 * | 9/2002 | Garner et al. | .................. | 210/348 |
| 2002/0188276 A1 * | 12/2002 | Evans et al. | ................... | 604/509 |
| 2003/0114911 A1 * | 6/2003 | Lupton | ........................ | 623/1.11 |
| 2008/0004652 A1 * | 1/2008 | Abboud et al. | ............... | 606/192 |
| 2008/0300539 A1 * | 12/2008 | Vreeman et al. | .......... | 604/103.06 |

FOREIGN PATENT DOCUMENTS

JP        2010/094229        4/2010

* cited by examiner

*Primary Examiner* — Michael N Orlando
*Assistant Examiner* — Marta Dulko

(57) ABSTRACT

The present invention relates to a catheter (1', 1") for intraluminal treatment which comprises a main tubular body (2) extending along a longitudinal axis (X) between a proximal end portion (2') and a distal end portion (2"), which delimits at least one central lumen (4). The main tubular body identifies at least one balloon (8). The catheter further comprises at least one inner tubular body (6), at least partially housed in the central lumen, which delimits at least one inner lumen (16) for housing at least one guide wire, the portion of distal extremity of the balloon being joined to the inner tubular body. Furthermore, the central axis (Y) of the inner lumen is arched or undulated to form an accumulation of material for the expansion of the balloon. The present invention further refers to a method of manufacturing the catheter of the invention and to a machine for the production of a tool used during the aforesaid method.

8 Claims, 3 Drawing Sheets

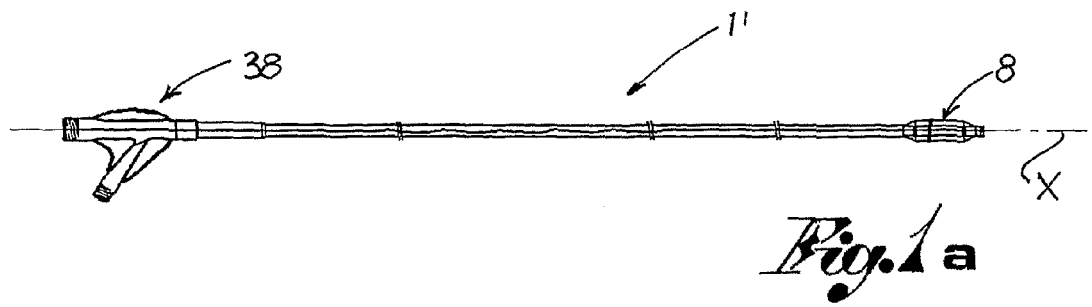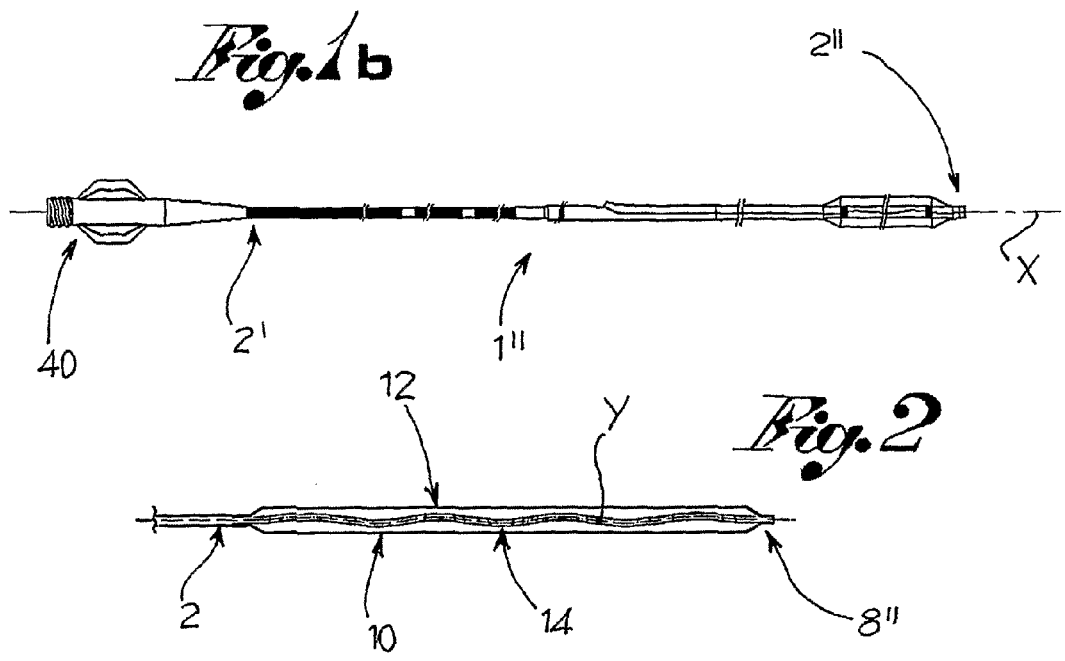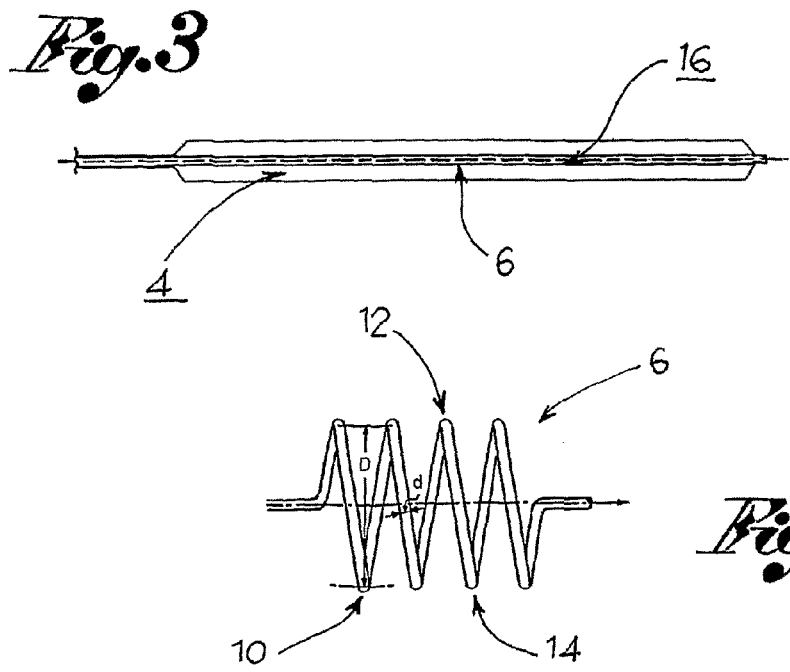

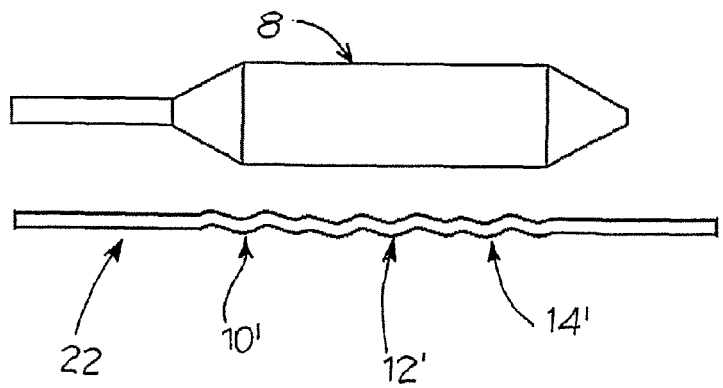
*Fig.5*
*Fig.6*
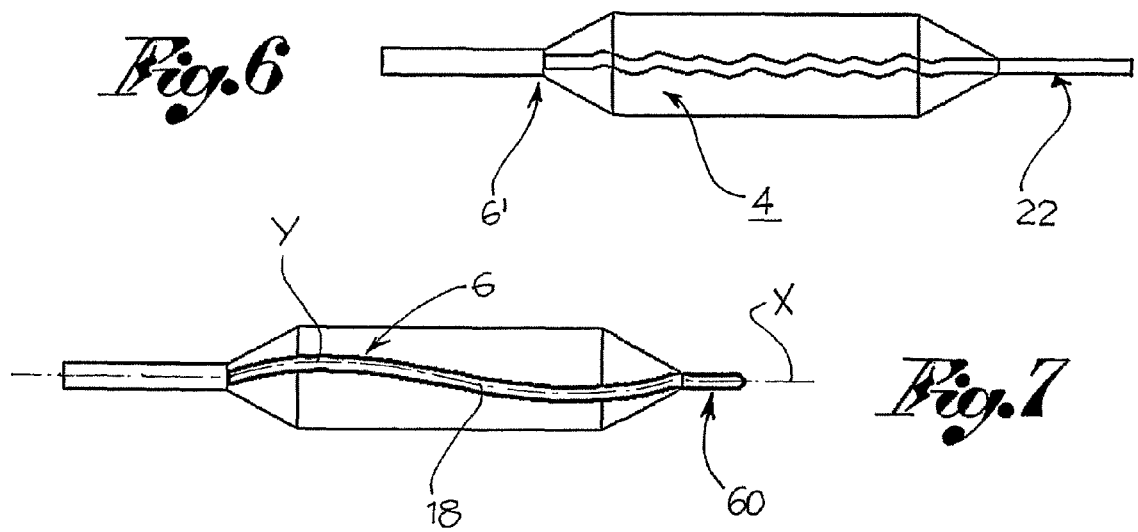
*Fig.7*
*Fig.8*
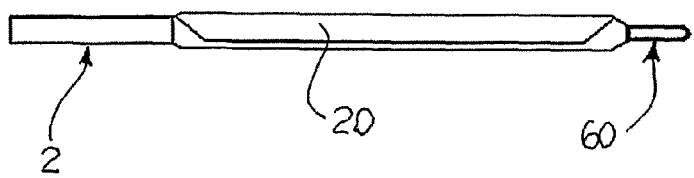
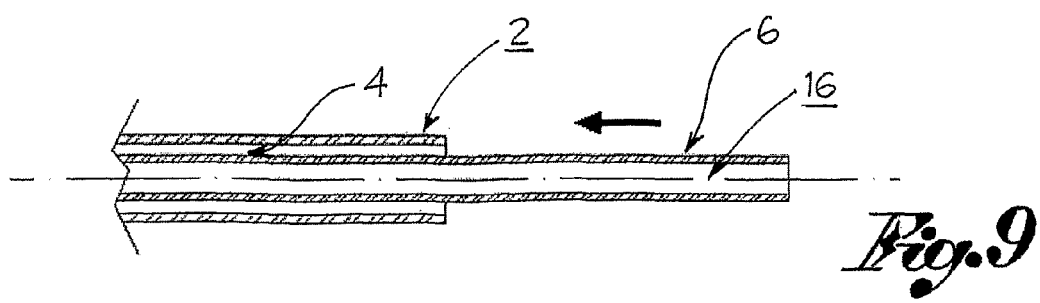
*Fig.9*

CATHETER FOR INTRALUMINAL TREATMENT, METHOD FOR MAKING THE SAME AND APPARATUS FOR MAKING A TOOL

The present invention relates to a catheter per intraluminal treatment, particularly suitable for reducing flexing of the balloon during expansion of the latter.

The use of catheters for intraluminal treatment in the human body is known in the art, e.g. to perform angioplasty operations or for positioning stents in arteries blocked by stenosis.

One type of such devices comprise an outer tubular body, which extends along a longitudinal axis and which identifies at least one central lumen, and at least one inner tubular body, at least partially housed in the central lumen.

The outer tubular body identifies, furthermore, at least one balloon having a portion of distal extremity joined to the inner tubular body and expandable between a rest configuration, in which the catheter is suitable for being conducted through an organic cavity, and an expanded configuration to perform the desired treatment.

One of the most widely felt difficulties in relation to the aforesaid devices is that, during inflation, the balloon undergoes a mainly radial expansion but also lengthens axially.

Such axial longitudinal lengthening of the balloon, despite being inferior to the radial expansion, makes the inner tubular body oppose the longitudinal extension of the balloon, essentially acting as a mechanical tie-rod.

As a result, the balloon of catheters with an inner tubular body not perfectly centred in the inflation compartment of the balloon tends to assume a curved configuration, such as that shown in FIG. 11, which is progressively more marked as it approaches, and even more when it exceeds, the nominal pressure for that balloon.

The phenomenon described, known as the "banana effect", may constitute a considerable source of risk for the patient, especially on account of the unforeseeable orientation of the balloon once it reaches the required pressure.

The devices illustrated in documents EP 1 896 110 B1 and US 2009/0036829 A1 have overcome the aforesaid technical drawback by fitting the inner tubular body with an elastic or bellows portion, therefore yielding axially so as to compensate the longitudinal lengthening of the balloon by axial straightening of the inner tubular body.

Despite the aforementioned expedients having been suitable for reducing onset of the banana effect, the solutions proposed in earlier documents achieve the desired longitudinal extensibility by means of at least one resilient portion of the inner tubular body.

The realisation of such resilient portion implies however special manufacturing steps increasing the complexity of the production process and consequently, the cost of the final product.

For example, document US 2009/0036829 A1 illustrates an annealing heat treatment to modify the elastic behaviour of the material which the inner tubular body is made of. Again, document EP 1 896 110 B1 creates a plurality of crimps on the inner tubular body necessarily requiring a modified manufacturing method compared to traditional processes.

The present invention sets out to supply a catheter suitable for reducing the banana effect described above, and furthermore suitable for being manufactured essentially using the same materials and methods used traditionally so as to keep production costs the same as for traditional catheters.

Such objective is achieved by a catheter according to claim 1, a method according to claim 14, and using a machine according to claim 24. The dependent claims show preferred embodiments.

The present invention will now be described with the help of the attached figures, wherein:

FIGS. 1a and 1b show two ground views of the catheter which the present invention relates to, in two possible variants, relative to an "over the wire" (OTW) variant and a "rapid exchange" (RX) variant respectively;

FIGS. 2 and 3 show two enlargements of the catheter in FIG. 1b, respectively in a rest configuration and in an expanded configuration, according to a possible embodiment;

FIG. 4 shows the first curvilinear sections of an inner tubular body according to a variant of the invention;

FIGS. 5 to 8 show different steps of the manufacturing process of the catheter which the invention relates to, in one variant;

FIG. 9 shows a variation of a manufacturing step of the catheter of the invention according to a further alternative;

Figure 10:
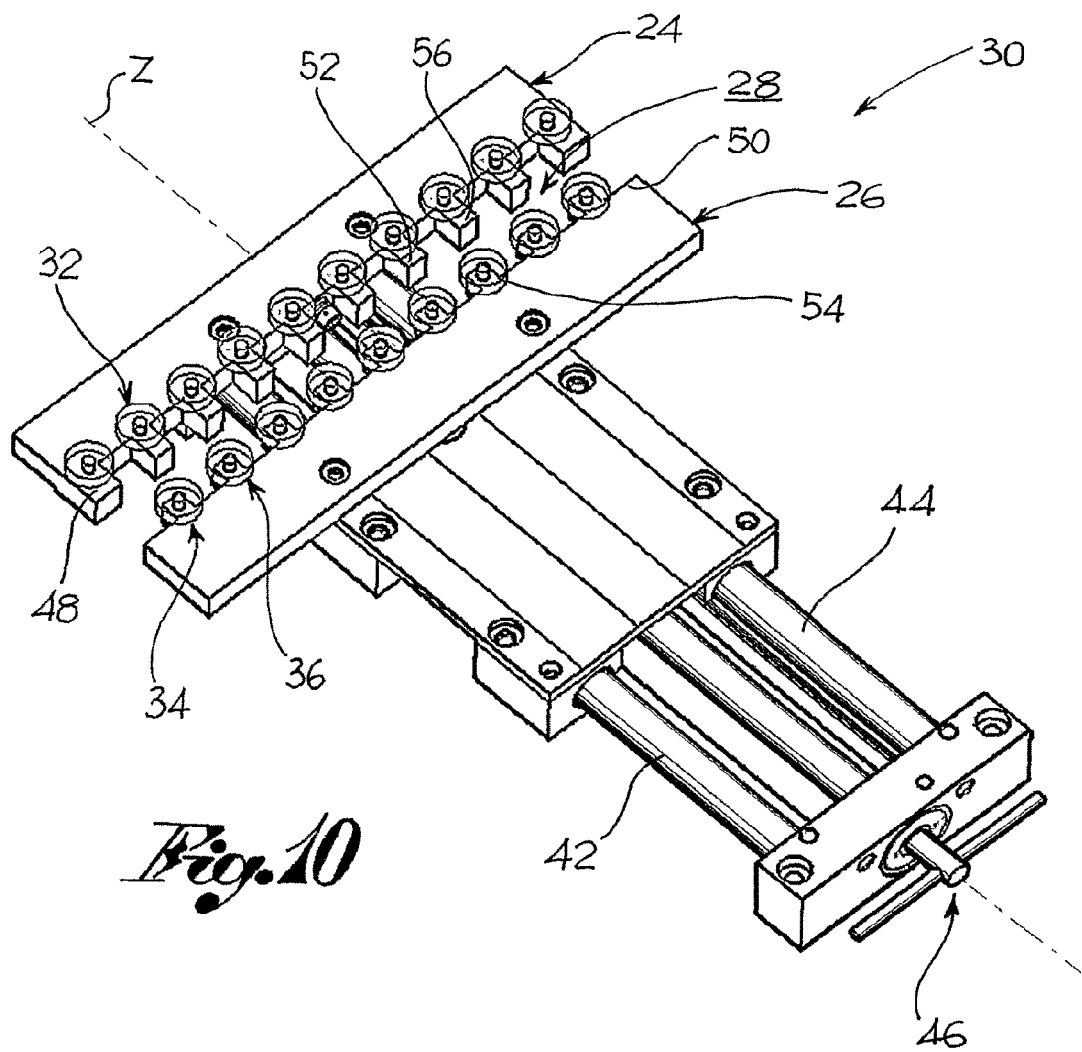
FIG. 10 shows a perspective view of a machine for manufacturing a tool for the realisation of a catheter according to the invention.
Figure 11:
FIG. 11 shows a state of the art catheter subject to the banana effect.

With reference to the attached tables, reference numeral 1', 1" globally denotes a catheter for intraluminal treatment.

Such treatment comprises, by way of a non-limiting example, an angioplasty procedure, positioning of a stent and so forth.

According to a preferred variant of the invention, the catheter 1', 1" is of the OTW type.

According to an alternative variant, the catheter 1', 1" is of the type having an RX port.

The catheter 1', 1" comprises a main tubular body 2, which extends along a longitudinal axis X between a proximal end portion 2' and a distal end portion 2" and which delimits at least one central lumen 4.

In other words, the main tubular body 2 encloses inside it at least one central lumen 4, which extends at least partially between the proximal end portion 2' and the distal end portion 2" of the body 2.

According to a preferred variant, the main tubular body 2 is bi-lumen, i.e. identifies a first and second central lumen (not shown).

In other words, the main tubular body 2 delimits the first and the second central lumen, which are separated by a wall of the tubular body which extends along the longitudinal axis X.

This way, fluidic communication between such lumen is prevented, respectively designed for the passage of the inflation fluid of the balloon and to house a guide wire.

According to one embodiment, the catheter 1', 1" further comprises at least one connector 38, 40, for example one-way (as illustrated in FIG. 1b), two-way (as shown in FIG. 1a) or three-way (not shown), joined to the proximal end portion 2' of the main tubular body 2.

By means of the connector 38, 40 therefore, the catheter 1', 1" can be operated by an operator, for example to dilate the balloon, or to conduct the catheter 1', 1" through organic cavities and, if necessary, their branches, as far as the site where intervention is required.

The main tubular body 2 identifies at least one balloon 8, which comprises a portion of distal extremity 8" and which is expandable between a rest configuration, wherein the catheter 1', 1" is suitable for being conducted through an organic cavity, and an expanded configuration.

The main tubular body 2 identifies, therefore, preferably at the portion of distal extremity 2", at least one balloon 8 which is inflatable or expandable between the aforesaid configurations.

In the rest configuration of the balloon 8, the latter has a moderate transversal dimension in relation to the longitudinal axis X, such as to permit transit of the catheter 1', 1" through the said organic cavity.

In other words, in the rest configuration, the balloon 8 is contracted, or in any case of limited encumbrance, such as not to obstruct passage of the catheter 1', 1" through the organic cavity.

In yet other terms, in the rest configuration, the balloon 8 has a radial dimension essentially coinciding with the dimension of the main tubular body 2 proximally to the balloon 8 itself.

Vice versa, in the expanded configuration, the balloon 8 has an increased radial dimension compared to the rest configuration.

As a result, in such second configuration, the outer surface of the balloon 8 extends radially beyond the surface of the main tubular body 2 proximally to the balloon 8 itself.

In other words, in the expanded configuration, the balloon 8 is at least partially filled with fluid, and consequently proves dilated by such fluid, to enable intraluminal treatment, such as positioning of a stent.

Consequently, in the expanded configuration of the balloon 8, the catheter 1', 1" is unsuitable for being conducted through the organic cavity given its radial dimension, except conditional to conversion of the balloon 8 to the rest configuration.

Preferably, the balloon 8 has a plurality of folds 20 (for example as illustrated in FIG. 8) which unfold for expansion of the balloon 8.

Consequently, in the rest configuration according to such variant, the balloon 8 has the folds 20, which represent folded portions of the balloon. Such folded portions are suitable, during conversion towards the expanded configuration, to distend to increase the inner volume of the balloon 8, for example so as to contain, a greater volume of the inflation fluid.

The catheter 1', 1" further comprises at least one inner tubular body 6, at least partially housed in the central lumen 4, which delimits at least one inner lumen 16 to house at least one guide wire.

Consequently, at least one portion of the inner tubular body 6, preferably a portion that is proximal 6' to the balloon 8, is housed in the main tubular body 2.

According to a preferred embodiment, the main tubular body 2 and the inner tubular body 6 are positioned so as to be reciprocally coaxial (coaxial configuration).

Furthermore, the inner lumen 16 identified by the inner tubular body 6 is suitable for housing the guide wire (not shown) for example in a slidable manner along the longitudinal axis X and/or in a rotatable manner around an axis essentially parallel to such axis X.

According to one variant, the inner tubular body 6 is composed of a material essentially inextensible up to the nominal pressure of the balloon 8 in the expanded configuration.

In the present description, the term "essentially inextensible" means that the material which the inner tubular body 6 is composed of permits a percentage lengthening of such body 6 of less than 1% of its overall length and, preferably, less than 0.5%.

Preferably, the inner tubular body 6 has at least one proximal portion 6' to the balloon 8 joined axially to the main tubular body 2.

In other words, according to such variant, the inner tubular body 6 is engaged in the main tubular body 2 in such a manner that such bodies 2, 6 are reciprocally blocked in an axial direction.

The portion of distal extremity 8" of the balloon 8 is further joined to the inner tubular body 6.

In other words, the balloon 8 has a portion of distal extremity 8", preferably the tail of such balloon 8, which is joined to the inner tubular body 6, preferably by welding, advantageously by means of laser-welding.

This way, the proximal portion 6' of the inner tubular body 6 is axially joined to the main tubular body 2, while another portion of the inner tubular body 6, preferably distanced axially distally from the proximal portion 6', is joined to the portion of distal extremity 8" of the balloon 8.

Furthermore, the central axis Y of the inner lumen 16 is arched or undulated to form an accumulation of material for the expansion of the balloon 8.

In other words, innovatively, the inner tubular body 6 has an excessive longitudinal extension such that, in the rest configuration of the balloon 8, a rectilinear arrangement of said inner tubular body 6 in the longitudinal space reserved for it is prevented.

In other words again, the inner tubular body 6 is of such length as to form at least a first curved section 10, 12, 14, preferably a plurality of such first sections, in relation to the longitudinal axis X.

Consequently, the length of the inner tubular body 6 being greater than the rectilinear distance between the proximal portion 6' of the inner tubular body 6 joined axially to the main tubular body 2 and the portion of the inner tubular body 6 joined to the portion of distal extremity 8" of the balloon 8, the inner tubular body 6 arranges itself in the central lumen 4 in a curved manner.

In the present patent, the term "central axis of the inner lumen" means the geometric locus of the centres of the transversal sections of the inner tubular body 6.

In other words, to construct the central axis Y of the inner tubular body a transversal section of the latter must be made, and at a point of a first edge of such section a first perpendicular line is identified which extends towards the edge opposite it; subsequently the bisector of the first perpendicular line is constructed, included between the two edges.

The aforesaid operation is repeated for a plurality of subsequent adjacent points, obtaining a number of bisectors. The line joining all the aforesaid bisectors constitutes the central axis Y of the inner lumen.

In other terms again, the inner tubular body extends longitudinally along an arched or undulated course, that is adopting an arched or undulated trend, said course or trend being indicated as the central axis Y.

According to a preferred variant, the central axis Y intersects the longitudinal axis X in at least one point 18, as illustrated for example in FIG. 7.

Preferably, the through section of the inner lumen 16 is distanced, preferably completely, from the longitudinal axis X.

In other words, the through section of the inner lumen 16 diverges at least partially from the longitudinal axis X so that the latter is not aligned with such section.

According to a particularly advantageous embodiment, the inner tubular body 6 comprises a plurality of first curvilinear sections 10, 12, 14 distanced along the longitudinal axis X, as illustrated for example in FIG. 2.

In such regard, advantageously, it has been estimated that an increased number of first curvilinear sections 10, 12, 14 enables a progressive reduction of the banana effect, as a result of the greater reserve of available material.

Preferably, the first curvilinear sections 10, 12, 14 are arranged helicoidally, for example with a fixed pitch or variable pitch D as shown in FIG. 4.

According to a further embodiment variation, schematised for example in FIG. 1b, the first curvilinear sections 10, 12, 14 are essentially contained in the central lumen 4 at the point of the inflation area identified by the balloon 8.

According to yet a further variant, for example schematised in FIG. 1a, the first curvilinear sections 10, 12, 14 are positioned in the central lumen 4 proximally to the balloon 8.

This last variant is particularly advantageous in cases in which a greater accumulation of material of the inner tubular body 6 needs to be made available, in that the aforesaid accumulation can be distributed along a greater distance of the tubular body.

Advantageously, the accumulation of material represents about 3-5% of the overall length of the inner tubular body 6 and, preferably, about 1-7%.

According to a preferred embodiment, the inner tubular body 6 is axially compressed. See FIG. 9 for example.

In other words, the inner tubular body 6 is pre-loaded inside the central lumen 4, so as not to counter the axial lengthening of the balloon 8 and, consequently, avoiding onset of the banana effect.

Pre-loading of the inner tubular body 6 is performed by a thrust action in a proximal axial direction by the operator during the production process, so that a greater length (a length in excess) can be provided for the inner tubular body 6 inside the main tubular body 2.

So, according to such variant, the tensional state of the inner tubular body 6 inside the central lumen 4 is of (pre-)compression so that, for the expansion of the balloon, the inner tubular body 6 relaxes, lengthening longitudinally.

Consequently, advantageously, the longitudinal extension of the balloon in the expanded configuration occurs in such a way as to second the condition which the inner tubular body is spontaneously inclined to assume, rather than oppose it as traditional catheters do.

The present invention also relates to a method for manufacturing a catheter, preferably a catheter 1', 1" according to any of the variants previously illustrated.

In an initial step of such method, a main tubular body 2 is provided, which extends along a longitudinal axis X between a proximal end portion 2' and a distal end portion 2" and which delimits at least one central lumen 4. Such step is illustrated, for example, in FIG. 5.

The main tubular body 2 identifies at least one balloon 8, which comprises a portion of distal extremity 8" and which is expandable between the rest configuration, wherein the catheter 1', 1" is suitable for being conducted through an organic cavity, and the expanded configuration.

In a subsequent step, at least one inner tubular body 6 is provided which delimits at least one inner lumen 16 to house at least one guide wire, and the inner tubular body 6 is at least partially housed in the central lumen 4 of the main tubular body 2.

So, the main tubular body 2 is penetrated by the inner tubular body 6, so that the latter is at least partially positioned in the central lumen 4.

In further steps according to the method, the inner tubular body 6 and the main tubular body 2 are axially proximally blocked, and the inner tubular body 6 is curved so as to create an accumulation of material for the expansion of the balloon 8.

So, in this step, the inner tubular body 6 is suitably and intentionally curved by a pre-defined extent.

In other words, during this step, the inner tubular body 6 is shaped in an undulated manner to create the aforesaid reserve (or accumulation) of material, i.e. the longitudinal axis of the inner tubular body assumes a curved or undulated, essentially non-rectilinear configuration.

Lastly, the portion of distal extremity 8" of the balloon 8 is joined, preferably tight, to the inner tubular body 6.

This way, during the expansion of the balloon, the accumulation of material is made available to prevent the banana effect described previously from being generated as a result of the longitudinal expansion of the balloon.

Preferably, the step of curving the inner tubular body 6 comprises a step of making at least one first curved section 10, 12, 14, preferably a plurality of such first sections 10, 12, 14.

Even more preferably, the step of curving comprises a step of housing at least partially in the inner lumen 16 a tool or mandrel 22 comprising at least one second curved section 10', 12', 14', as shown in FIG. 5.

So, the mandrel 22 is at least partially housed in the inner lumen 16 so that the second curved section 10', 12', 14' of such mandrel 22 imposes its course on the inner tubular body 6, that is to say forming on the latter the first curved section 10, 12, 14 of a corresponding shape, as illustrated in FIG. 6.

The variant which foresees use of the mandrel 22 having second curvilinear sections 10', 12', 14' is particularly advantageous for the embodiments in which the main tubular body 2 is bi-lumen.

Preferably, the mandrel 22 identifies an even, whole number of second curved sections 10', 12', 14'.

According to a further variant, the method further comprises a step of removing the mandrel 22 from the inner lumen 16.

Such step of removing is preferably accompanied by a rearranging of the inner tubular body 6. In particular, according to the variant illustrated in FIG. 7, the tubular body 6 positions itself in the central lumen 4 in an essentially random manner, and its longitudinal axis assumes an essentially non-rectilinear configuration. Alternatively, the inner tubular body 6 assumes the helicoidal conformation illustrated in FIG. 4. Such second conformation is preferably obtained through a step of heat-moulding, performed using a mandrel having a helicoidal conformation.

Advantageously, such step of heat-moulding can be avoided in the production processes as per FIG. 5 and FIG. 9.

Preferably, the step of removing takes place subsequently to the step of joining the portion of distal extremity 8" of the balloon 8 to the inner tubular body 6.

This way, advantageously, the mandrel 22 acts as a support for the connection of the balloon 8 and the inner tubular body 6, preventing the latter from being deformed as a result of any pressure exerted radially internally to consolidate the connection.

Preferably, the step of joining the portion of distal extremity 8" of the balloon 8 comprises a step of welding, advantageously of laser-welding.

This way, by means of the at least partial softening of the materials which the balloon 8 and the inner tubular body 6 are made of, the attachment is tight, stable and definitive.

Advantageously, the step of welding comprises a step of rotating the balloon 8 around an axis essentially parallel to the longitudinal axis X.

For the embodiments which foresee both the use of a mandrel 22 with an even, whole number of second curvilinear sections 10', 12', 14' and a step of rotating of the balloon 8 around the longitudinal axis X, it is particularly advantageous for such mandrel to contribute substantially to keeping the catheter balanced during welding, making it possible to prevent harmful transversal oscillation from jeopardising the reliability of the weld.

According to an advantageous variant, the step of joining comprises a step of joining a catheter tip 60 to the catheter 1', 1''.

This way, advantageously, e.g. in a single welding operation, it is possible to join both the balloon 8 to the inner tubular body 6, and the catheter tip 60 to the balloon 8 or to the inner tubular body.

According to a particularly advantageous variant, the step of curving comprises a step of axially compressing the inner tubular body 6.

In other words, according to such variant, before performing the step of joining the portion of distal extremity 8'' of the balloon 8 to the inner tubular body 6, the latter is compressed or pushed inside the central lumen 4 so as to achieve a more favourable tensional state of the inner tubular body 6 for the expansion of the balloon 8.

According to a further variant, the step of axial compression comprises a step of at least partially housing an essentially rectilinear tool or mandrel in the inner lumen 16.

Such variant is particularly advantageous for the embodiments in which the main tubular body 2 and the inner tubular body 6 are positioned reciprocally coaxially.

According to one embodiment, the method further comprises a step of shaping the balloon 8 into a plurality of folds 20 suitable for unfolding for its expansion. Such step is known in the trade by the term "balloon folding".

The present invention also relates to a machine 30 for making a tool or mandrel 22 such as that just described.

Such machine 30 comprises a first 24 and a second deformation element 26, suitable for housing between them at least a portion of a mandrel 22, wherein at least one of such elements 24, 26 is movable in relation to the other along a direction of movement Z.

In other words, the at least two deformation elements 24, 26 identify between them a seat for the positioning of at least one portion of the mandrel 22, and at least one of such deformation elements, the first 24 or the second 26, is moveable in relation to the other, the second 26 or the first 24, along the direction of movement Z.

According to some variants, such movement takes place by means of motor (not shown) or manual means, such as a two arm lever 46 operable by a user (FIG. 10).

Such movement takes place between a non-use configuration for housing the mandrel 22, and a deformation configuration, wherein such elements 24, 26 identify an at least partially winding course 28 for the deformation of the mandrel 22.

So, in the non-use configuration, the deformation elements 24, 26 are positioned in such a manner as to enable housing of the mandrel 22 between them, while in the deformation configuration, the deformation elements 24, 26 identify the course 28 which essentially corresponds to the desired conformation of the mandrel 22 subsequent to operation of the machine 30.

In other words, in the movement towards the deformation configuration, the deformation elements 24, 26 are suitable for exerting on the mandrel 22 a deformation force to convert it to the desired shape.

Preferably, the mobile deformation element 24, 26 slides along at least one translation guide 42, 44 between the configurations described.

The first deformation element 24 comprises at least one first roller or abutment 32 for the mandrel 22, and the second deformation element 26 comprises at least one pair of second rollers or abutments 34, 36 staggered in relation to the first roller 32 in a direction transversal to the direction of movement Z.

According to one variant, such first 32 and second rollers 34, 36 are of the same diameter.

Preferably, the pair of second rollers 34, 36 is staggered in relation to the first roller 32 in a direction essentially orthogonal to the direction of movement Z.

Even more preferably, the pair of second rollers 34, 36 is staggered in relation to the first roller 32 by at least one and a half times the diameter of the latter.

In other words, the space between each second roller 34, 36 and the centre of the first roller 32 is at least one and a half times the diameter of the latter.

Furthermore, the second rollers 34, 36 are reciprocally distanced so that the first roller 32 is suitable for being at least partially housed between them 34, 36, to obtain an arched or undulated tool 22.

In other words, in the deformation configuration, the first roller 32 positions itself between the second rollers 34, 36 in such a way as to identify the course 28 with them.

According to a particularly advantageous variant, the edges 48, 50 of the deformation elements 24, 26 which face each other have an irregular profile, i.e. comprising a plurality of support teeth 52, 54, 56, 58.

Preferably, such edges 48, 50 have complementary profiles.

Even more preferably, the rollers 32, 34, 36 are joined to the respective deformation elements 24, 26 in a detachable manner.

Consequently, such rollers 32, 34, 36 are suitable for being rapidly replaced in the case of wear but, above all, they can be assembled/dismantled in an extremely versatile manner.

According to the above description, indeed, in some circumstances it is preferable to have available a greater reserve of material for the inner tubular body 6; in such case a mandrel 22 must be made with a greater number of second curvilinear sections 10', 12', 14'; it will therefore be opportune to provide the machine 30 with an increased number of rollers 32, 34, 36.

The opposite is also true, where a lesser reserve of material may be achieved by removing a suitable number of rollers 32, 34, 36.

According to a preferred variant, each roller 32, 34, 36 is connected at the point of a respective support tooth 52, 54, 56, 58.

Innovatively, the catheter which the present invention relates to makes it possible to reduce the banana effect which occurs in the known catheters, and furthermore it is suitable for being manufactured essentially using the same materials and methods traditionally employed so as to keep production costs unchanged in relation to the traditional catheters.

Advantageously, the method which the present invention relates to makes it possible to make catheters having different reserves of material, so as to be suitable for any application.

A person skilled in the art may make variations or replacements of elements with others functionally equivalent to the aforesaid embodiments of the catheter, method and machine so as to satisfy specific requirements.

Such variations are also contained within the sphere of protection as defined by the following claims.

Furthermore, each variant described as belonging to a possible embodiment may be realised independently of the other variants described.

The invention claimed is:

1. A catheter for an intraluminal treatment comprising:
an elongate main tubular body having a central lumen and a longitudinal axis (X);
an inner tubular body having:
   a guide wire lumen extending through the inner tubular body, wherein the guidewire lumen defines a central axis (Y) therethrough;
   a first proximal portion forming a joint with the main tubular body;
   a second portion distanced axially distally from the joint; and
   a third portion extending between the first and second portions, wherein the guidewire lumen extends through the first proximal portion, the second portion, and third portion of the inner tubular body; and
a balloon comprising a portion of the main tubular body extending from the joint to a balloon distal tail joined to the second portion of the inner tubular body and surrounding the third portion of the inner tubular body, wherein the guide wire lumen extending through the inner tubular body is the only lumen located within the balloon, the balloon being expandable between a rest configuration suitable for being conducted through an organic cavity and a radially and longitudinally expanded configuration;
wherein, when the balloon is in the rest configuration, the third portion of the inner tubular body including the central axis (Y) has a pre-defined shape of an arch or undulation.

2. A catheter according to claim 1, wherein the central axis (Y) intersects the longitudinal axis (X) in at least one point.

3. A catheter according to claim 1, wherein the central axis (Y) is distanced from the longitudinal axis (X).

4. The catheter according to claim 3 wherein the central axis (Y) is distanced from the longitudinal axis (X) by at least one diameter (d) of the inner tubular body.

5. The catheter according to claim 1 wherein the third portion of the inner tubular body comprises a plurality of first curvilinear sections.

6. The catheter according to claim 5, wherein the first curvilinear sections are arranged helicoidally with a fixed or variable pitch (D).

7. The catheter according to claim 1 wherein the third portion of the inner tubular body is axially compressed when the balloon is in the rest configuration.

8. A catheter according to claim 1, wherein the pre-defined shape of an arch or undulation has been obtained by heat-molding the inner tubular body when the balloon is in the expanded configuration, the first proximal portion and the second portion of the inner tubular body are farther apart from each other along the longitudinal axis (X) than when the balloon is in the rest configuration.

* * * * *